United States Patent
Tan et al.

(10) Patent No.: US 9,814,668 B2
(45) Date of Patent: *Nov. 14, 2017

(54) HAIR STYLING COMPOSITIONS COMPRISING LATEX POLYMERS

(71) Applicant: L'OREAL, Paris (FR)

(72) Inventors: Siliu Tan, Westfield, NJ (US); Aditi Gogineni, Rahway, NJ (US); Jean-Thierry Simonnet, Rueil Malmaison (FR); Jim Mitchell Singer, South Orange, NJ (US); Nghi Van Nguyen, Edison, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/576,639

(22) Filed: Dec. 19, 2014

(65) Prior Publication Data

US 2016/0175236 A1    Jun. 23, 2016

(51) Int. Cl.
  *A61Q 5/06*   (2006.01)
  *A61K 8/895*  (2006.01)
  *A61K 8/81*   (2006.01)
  *A61K 8/87*   (2006.01)
  *A61K 8/04*   (2006.01)

(52) U.S. Cl.
  CPC ............. *A61K 8/895* (2013.01); *A61K 8/044* (2013.01); *A61K 8/8141* (2013.01); *A61K 8/87* (2013.01); *A61Q 5/06* (2013.01)

(58) Field of Classification Search
  None
  See application file for complete search history.

(56) References Cited

U.S. PATENT DOCUMENTS

| | | | |
|---|---|---|---|
| 3,110,695 A | 11/1963 | Ceresa | |
| 3,304,273 A | 2/1967 | Stamberger | |
| 3,383,351 A | 5/1968 | Paul | |
| 3,412,054 A | 11/1968 | Milligan et al. | |
| 3,523,095 A | 8/1970 | James et al. | |
| 3,915,921 A | 10/1975 | Schlatzer, Jr. | |
| 4,003,699 A | 1/1977 | Rose et al. | |
| RE30,199 E | 1/1980 | Rose et al. | |
| 4,509,949 A | 4/1985 | Huang et al. | |
| 4,644,030 A | 2/1987 | Loewrigkeit et al. | |
| 4,710,374 A | 12/1987 | Grollier et al. | |
| 4,798,721 A | 1/1989 | Yahagi et al. | |
| 4,985,239 A | 1/1991 | Yahagi et al. | |
| 5,061,289 A | 10/1991 | Clausen et al. | |
| 5,085,859 A | 2/1992 | Halloran et al. | |
| 5,156,911 A | 10/1992 | Stewart | |
| 5,173,526 A | 12/1992 | Vijayendran et al. | |
| 5,221,534 A | 6/1993 | DesLauriers et al. | |
| 5,380,340 A | 1/1995 | Neunhoeffer et al. | |
| 5,441,728 A | 8/1995 | Tsaur et al. | |
| 5,534,267 A | 7/1996 | Neunhoeffer et al. | |
| 5,565,216 A | 10/1996 | Cowsar et al. | |
| 5,618,523 A | 4/1997 | Zysman et al. | |
| 5,637,291 A | 6/1997 | Bara et al. | |
| 5,663,366 A | 9/1997 | Neunhoeffer et al. | |
| 5,679,327 A | 10/1997 | Darkwa et al. | |
| 5,708,151 A | 1/1998 | Moeckli | |
| 5,753,215 A | 5/1998 | Mougin et al. | |
| 5,766,576 A | 6/1998 | Lowe et al. | |
| 5,932,194 A | 8/1999 | Plessix et al. | |
| 6,013,682 A | 1/2000 | Dalle et al. | |
| 6,099,592 A | 8/2000 | Vidal et al. | |
| 6,110,451 A | 8/2000 | Matz et al. | |
| 6,120,778 A | 9/2000 | Simonnet | |
| 6,126,929 A | 10/2000 | Mougin | |
| 6,126,948 A | 10/2000 | Simonnet et al. | |
| 6,165,446 A | 12/2000 | Samain et al. | |
| 6,214,328 B1 * | 4/2001 | Chang et al. | 424/70.16 |
| 6,268,431 B1 | 7/2001 | Snyder et al. | |
| 6,284,003 B1 | 9/2001 | Rose et al. | |
| 6,338,741 B1 | 1/2002 | Vidal et al. | |
| 6,399,050 B1 | 6/2002 | Pasquet et al. | |
| 6,464,990 B2 | 10/2002 | Simonnet et al. | |
| 6,482,394 B1 | 11/2002 | Schehlmann et al. | |
| 6,585,965 B1 | 7/2003 | Carballada et al. | |
| 6,592,633 B2 | 7/2003 | Lang et al. | |
| 6,613,315 B1 | 9/2003 | Dupuis | |
| 6,645,258 B2 | 11/2003 | Vidal et al. | |
| 6,703,028 B1 | 3/2004 | Samain et al. | |

(Continued)

FOREIGN PATENT DOCUMENTS

| | | |
|---|---|---|
| DE | 1152536 B | 8/1963 |
| DE | 2359399 A1 | 6/1975 |

(Continued)

OTHER PUBLICATIONS

Co-pending U.S. Appl. No. 14/577,579, Siliu Tan et al., "Hair Styling Compositions Comprising Latex Polymers and Wax Dispersions," filed Dec. 19, 2014.
Co-pending U.S. Appl. No. 14/578,074, Siliu Tan et al., "Compositions and Methods for Hair," filed Dec. 19, 2014.
Co-pending U.S. Appl. No. 14/577,740, Christine Shin et al., "Hair Cosmetic Composition Containing Latex Polymers and a Silicone-Organic Polymer Compound," filed Dec. 19, 2014.
Co-pending U.S. Appl. No. 14/577,809, Mark Benn, "Hair Coloring Compositions Comprising Latex Polymers," filed Dec. 19, 2014.
Co-pending U.S. Appl. No. 14/586,105, Siliu Tan et al., "Compositions and Methods for Hair," filed Dec. 30, 2014.
Co-pending U.S. Appl. No. 14/578,122, Christine Shin, "Hair Cosmetic Composition Containing a Polyurethane Latex Polymer and a Silicone Organic Polymer Compound," filed Dec. 19, 2014.
Co-pending U.S. Appl. No. 13/931,329; Siliu Tan et al., "Compositions and Methods for Treating Hair," filed Jun. 28, 2013.

(Continued)

*Primary Examiner* — Jyothsna Venkat
(74) *Attorney, Agent, or Firm* — The Marbury Law Group, PLLC

(57) ABSTRACT

Disclosed are compositions comprising one or more latex polymers selected from acrylate latex, polyurethane latex polymers, and mixtures thereof, a dispersion of particles of at least one silicone latex polymer; and optionally, a solvent. Methods of using the compositions on keratinous substrates such as hair are also disclosed.

17 Claims, No Drawings

(56) References Cited

U.S. PATENT DOCUMENTS

| | | |
|---|---|---|
| 6,726,916 B1 | 4/2004 | Ramin |
| 6,730,789 B1 | 5/2004 | Birault et al. |
| 6,946,123 B2 | 9/2005 | De La Poterie et al. |
| 7,211,244 B2 | 5/2007 | Auguste et al. |
| 7,651,693 B2 | 1/2010 | Merlau et al. |
| 7,740,832 B1 | 6/2010 | Rollat-Corvol et al. |
| 7,785,613 B2 | 8/2010 | Collin et al. |
| 7,993,632 B2 | 8/2011 | Lezer et al. |
| 8,343,238 B1 | 1/2013 | Lopez et al. |
| 8,398,961 B2 | 3/2013 | Kaplan et al. |
| 8,691,200 B2 | 4/2014 | Vilbert |
| 8,865,147 B2 | 10/2014 | Rizk et al. |
| 2002/0007521 A1 | 1/2002 | Lang et al. |
| 2002/0010970 A1 | 1/2002 | Cottard et al. |
| 2002/0022009 A1 | 2/2002 | De La Poterie et al. |
| 2002/0050013 A1 | 5/2002 | Vidal et al. |
| 2002/0055562 A1 | 5/2002 | Butuc |
| 2002/0198328 A1 | 12/2002 | L'Alloret |
| 2003/0019051 A9 | 1/2003 | Vidal et al. |
| 2003/0026815 A1 | 2/2003 | Scott et al. |
| 2003/0044440 A1 | 3/2003 | Toumi |
| 2003/0053976 A1 | 3/2003 | Tournilhac et al. |
| 2003/0059377 A1 | 3/2003 | Riley |
| 2003/0059388 A1 | 3/2003 | Auguste et al. |
| 2003/0064045 A1 | 4/2003 | Tournilhac et al. |
| 2003/0103927 A1 | 6/2003 | Maubru |
| 2003/0138465 A9 | 7/2003 | Douin et al. |
| 2003/0147832 A1 | 8/2003 | L'Alloret |
| 2003/0161804 A1 | 8/2003 | Perron et al. |
| 2004/0071646 A1 | 4/2004 | Pataut et al. |
| 2004/0096474 A1 | 5/2004 | Merlau et al. |
| 2004/0214913 A1 | 10/2004 | L'Alloret |
| 2005/0008605 A1 | 1/2005 | L'Alloret |
| 2005/0020779 A1 | 1/2005 | Mougin et al. |
| 2005/0025736 A1 | 2/2005 | Jachowicz et al. |
| 2005/0048016 A1 | 3/2005 | Lebreton et al. |
| 2005/0053568 A1 | 3/2005 | Aubrun-Sonneville et al. |
| 2005/0065253 A1 | 3/2005 | Collin et al. |
| 2005/0089490 A1 | 4/2005 | Jachowicz et al. |
| 2006/0115446 A1 | 6/2006 | Rollat-Corvol et al. |
| 2006/0134043 A1 | 6/2006 | Nakamura |
| 2006/0182702 A1 | 8/2006 | Lazzeri et al. |
| 2006/0292095 A1 | 12/2006 | Biatry et al. |
| 2007/0031361 A1 | 2/2007 | Herrmann et al. |
| 2007/0190008 A1 | 8/2007 | Campain et al. |
| 2007/0224140 A1 | 9/2007 | Quadir et al. |
| 2007/0286833 A1 | 12/2007 | Keller et al. |
| 2008/0138307 A1 | 6/2008 | Bazemore et al. |
| 2008/0175808 A1 | 7/2008 | Pavel |
| 2008/0305064 A1 | 12/2008 | Bui et al. |
| 2009/0035335 A1 | 2/2009 | Marotta et al. |
| 2009/0060858 A1 | 3/2009 | Schwarzwaelder et al. |
| 2009/0074695 A1 | 3/2009 | Mahe et al. |
| 2009/0280076 A1 | 11/2009 | Yoshida et al. |
| 2009/0297467 A1 | 12/2009 | Laurent et al. |
| 2009/0317432 A1 | 12/2009 | Kergosien |
| 2010/0028284 A1 | 2/2010 | Atis et al. |
| 2010/0119467 A1 | 5/2010 | Dumousseaux et al. |
| 2010/0189678 A1 | 7/2010 | Knappe et al. |
| 2010/0278770 A1 | 11/2010 | Arditty et al. |
| 2011/0014139 A1 | 1/2011 | Viala et al. |
| 2011/0015279 A1 | 1/2011 | Doerr et al. |
| 2011/0097289 A1 | 4/2011 | Viala et al. |
| 2011/0097293 A1 | 4/2011 | Grey et al. |
| 2011/0150802 A1 | 6/2011 | Bui et al. |
| 2011/0150807 A1 | 6/2011 | Bui et al. |
| 2012/0247500 A1 | 10/2012 | Plos et al. |
| 2012/0282309 A1 | 11/2012 | Dihora et al. |
| 2012/0308496 A1 | 12/2012 | Viala et al. |
| 2013/0084256 A1 | 4/2013 | Li et al. |
| 2013/0167863 A1 | 7/2013 | Schmelz et al. |
| 2013/0171084 A1 | 7/2013 | Kawaratani et al. |
| 2013/0284198 A1 | 10/2013 | Rizk et al. |
| 2014/0102468 A1 | 4/2014 | Pistorio et al. |
| 2014/0105845 A1 | 4/2014 | Bui et al. |
| 2014/0105945 A1 | 4/2014 | Bui et al. |
| 2014/0186270 A1 | 7/2014 | Suleiman et al. |
| 2015/0004119 A1 | 1/2015 | Tan et al. |

FOREIGN PATENT DOCUMENTS

| | | |
|---|---|---|
| DE | 2364398 A1 | 10/1975 |
| DE | 3843892 A1 | 6/1990 |
| DE | 4133957 A1 | 4/1993 |
| DE | 19543988 A1 | 5/1997 |
| DE | 102009054516 A1 | 6/2011 |
| EP | 0216479 A1 | 4/1987 |
| EP | 0692237 A1 | 1/1996 |
| EP | 0714954 A2 | 6/1996 |
| EP | 0770375 A1 | 5/1997 |
| EP | 0847752 A1 | 6/1998 |
| EP | 0874017 A2 | 10/1998 |
| EP | 0898958 A1 | 3/1999 |
| EP | 0898960 A1 | 3/1999 |
| EP | 1082953 A1 | 3/2001 |
| EP | 1291051 A2 | 3/2003 |
| EP | 1466588 A1 | 10/2004 |
| EP | 1652509 A2 | 5/2006 |
| EP | 2356981 A1 | 8/2011 |
| EP | 2570192 A1 | 3/2013 |
| FR | 2633940 B3 | 7/1991 |
| FR | 2733749 A1 | 11/1996 |
| FR | 2774899 A1 | 8/1999 |
| FR | 2801308 A1 | 5/2001 |
| FR | 2834458 A1 | 7/2003 |
| FR | 2856923 A1 | 1/2005 |
| FR | 2889943 A1 | 3/2007 |
| FR | 2898050 A1 | 9/2007 |
| FR | 2961103 A1 | 12/2011 |
| FR | 2968978 A1 | 6/2012 |
| GB | 1026978 A | 4/1966 |
| GB | 1040452 A | 8/1966 |
| GB | 1153196 A | 5/1969 |
| JP | H021956 A | 1/1990 |
| JP | H05163124 A | 6/1993 |
| KR | 20100105168 A | 9/2010 |
| WO | 9408969 A1 | 4/1994 |
| WO | 9408970 A1 | 4/1994 |
| WO | 9501772 A1 | 1/1995 |
| WO | 9515144 A1 | 6/1995 |
| WO | 9615765 A1 | 5/1996 |
| WO | 0119333 A1 | 3/2001 |
| WO | 2005100444 A1 | 10/2005 |
| WO | 2007/102972 A1 | 9/2007 |
| WO | 2007099269 A2 | 9/2007 |
| WO | 2010133658 A2 | 11/2010 |
| WO | 2011056332 A1 | 5/2011 |
| WO | 2011069786 A2 | 6/2011 |
| WO | 2011137338 A2 | 11/2011 |
| WO | 2012049146 A2 | 4/2012 |
| WO | 2012/072774 A1 | 6/2012 |
| WO | 2013059106 A1 | 4/2013 |
| WO | 2013074210 A1 | 5/2013 |
| WO | 2013092378 A1 | 6/2013 |
| WO | 2013092379 A1 | 6/2013 |
| WO | 2013092380 A1 | 6/2013 |
| WO | 2013092381 A1 | 6/2013 |
| WO | 2013092382 A1 | 6/2013 |
| WO | 2013092562 A1 | 6/2013 |
| WO | 2013092779 A2 | 6/2013 |
| WO | 2013092788 A1 | 6/2013 |
| WO | 2014001390 A1 | 1/2014 |
| WO | 2014001391 A1 | 1/2014 |
| WO | 2014/058856 A1 | 4/2014 |
| WO | 2014/062334 A1 | 4/2014 |
| WO | 2014071354 A1 | 5/2014 |
| WO | 2014124066 A1 | 8/2014 |

OTHER PUBLICATIONS

Co-pending U.S. Appl. No. 13/931,187; Siliu Tan et al., "Compositions and Methods for Treating Hair," filed Jun. 28, 2013.

(56) References Cited

OTHER PUBLICATIONS

Co-pending U.S. Appl. No. 13/931,204; Siliu Tan et al., "Compositions and Methods for Treating Hair," filed Jun. 28, 2013.
Co-pending U.S. Appl. No. 13/931,222; Siliu Tan et al., "Compositions and Methods for Treating Hair," filed Jun. 28, 2013.
Co-pending U.S. Appl. No. 13/931,238; Siliu Tan et al., "Compositions and Methods for Treating Hair," filed Jun. 28, 2013.
Co-pending U.S. Appl. No. 13/931,248; Siliu Tan et al., "Compositions and Methods for Treating Hair," filed Jun. 28, 2013.
Co-pending U.S. Appl. No. 13/931,260; Siliu Tan et al., "Compositions and Methods for Treating Hair," filed Jun. 28, 2013.
Co-pending U.S. Appl. No. 13/931,276; Siliu Tan et al., "Compositions and Methods for Treating Hair," filed Jun. 28, 2013.
Co-pending U.S. Appl. No. 13/931,288; Siliu Tan et al., "Compositions and Methods for Treating Hair," filed Jun. 28, 2013.
Co-pending U.S. Appl. No. 13/931,298; Siliu Tan et al., "Compositions and Methods for Treating Hair," filed Jun. 28, 2013.
Co-pending U.S. Appl. No. 13/931,312; Siliu Tan et al., "Compositions and Methods for Treating Hair," filed Jun. 28, 2013.
English language abstract for EP 0770375 (May 2, 1997).
English language abstract for EP0898960 (Mar. 3, 1999).
English language abstract for EP1082953 (Mar. 14, 2001).
English language abstract for FR2633940 (Jul. 12, 1991).
English language abstract for FR2898050 (Sep. 7, 2007).
English language abstract for FR2968978 (Jun. 22, 2012).
English language Abstract of FR2834458 (Jul. 11, 2003).
Galgoci, Ernest C., et al., "Solvent-Free Urethane-Acrylic Hybrid Polymers for Coatings," JCT Coatings Tech, 2 (13), Feb. 2005, pp. 28-36.
International Search Report for Application No. PCT/US2014/044036, dated Oct. 21, 2014, 3 pages.
International Search Report for Application No. PCT/US2014/044377, dated Oct. 31, 2014, 3 pages.
International Search Report for Application No. PCT/US2014/044557, dated Oct. 13, 2014, 3 pages.
International Search Report for Application No. PCT/US2014/044587, dated Oct. 31, 2014, 3 pages.
International Search Report for Application No. PCT/US2014/044610, dated Oct. 31, 2014, 4 pages.
Jachowicz, J., et al., "Mechanical Analysis of Elasticity and Flexibility of Virgin and Polymer-Treated Hair Fiber Assemblies," J. Cosmet. Sci., 53, Nov./Dec. 2002, pp. 345-361.
Non-Final Office Action for U.S. Appl. No. 13/931,187, dated Feb. 13, 2015.
Non-Final Office Action for U.S. Appl. No. 13/931,204, dated Feb. 20, 2015.
Non-Final Office Action for U.S. Appl. No. 13/931,238, dated Feb. 13, 2015.
Non-Final Office Action for U.S. Appl. No. 13/931,248, dated Feb. 20, 2015.
Non-Final Office Action for U.S. Appl. No. 13/931,260, dated Feb. 20, 2015.
Non-Final Office Action for U.S. Appl. No. 13/931,276, dated Feb. 17, 2015.
Non-Final Office Action for U.S. Appl. No. 13/931,288, dated Feb. 18, 2015.
Non-Final Office Action for U.S. Appl. No. 13/931,298, dated Feb. 20, 2015.
Non-Final Office Action for U.S. Appl. No. 13/931,312, dated Feb. 18, 2015.
Non-Final Office Action for U.S. Appl. No. 13/931,329, dated Feb. 13, 2015.
Polyquats As Conditioning Agents, 2009. Retrieved from the Internet.
English language abstract for DE 102009054516 (Jun. 16, 2011).
English language abstract for EP 0847752 (Jun. 17, 1998).
English language abstract for FR 2961103 (Dec. 16, 2011).
English language abstract for JP H05-163124 (Jun. 29, 1993).
English language abstract for KR 20100105168 (Sep. 29, 2010).
Final Office Action for co-pending U.S. Appl. No. 13/931,187 (Jul. 20, 2015).
Non-Final Office Action for co-pending U.S. Appl. No. 13/931,222 (Apr. 7, 2015).
Non-Final Office Action for co-pending U.S. Appl. No. 14/577,809 (Jul. 10, 2015).
English language abstract for JP H021956 (Jan. 8, 1990).
Final Office Action for co-pending U.S. Appl. No. 13/931,222 (Jul. 28, 2015).
International Search Report and Written Opinion for counterpart Application PCT/US2015/065967, mailed Jul. 5, 2016.
International Search Report and Written Opinion for counterpart Application PCT/US2015/065975, mailed Jul. 5, 2016.
International Search Report and Written Opinion for copending Application No. PCT/US2015/066818, mailed Feb. 26, 2016.
Extended European Search Report for counterpart EP Application No. 14817057.4, mailed Nov. 2, 2016.
Extended European Search Report for counterpart EP Application No. 14818467.4, mailed Nov. 9, 2016.
Extended European Search Report for counterpart EP Application No. 14818460.9, mailed Nov. 21, 2016.
Extended European Search Report for counterpart EP Application No. 14817786.8, mailed Oct. 14, 2016.

\* cited by examiner

HAIR STYLING COMPOSITIONS COMPRISING LATEX POLYMERS

FIELD OF THE INVENTION

The disclosure relates to cosmetic compositions comprising one or more latex polymers and a dispersion of particles of at least one silicone latex polymer.

BACKGROUND OF THE INVENTION

Consumer products such as cosmetics, personal care, and household products, as well as pharmaceutical and industrial products, employ ingredients that allow these products to form a film or coating on various substrates such as keratinous substrates (e.g., hair and skin), hard surfaces (e.g., wood and metal), and other non-keratinous substrates, (e.g., fabrics and articles). Those ingredients which help form a film or coating on the surface of a substrate may be chosen from a variety of raw materials such as waxes, polymers, resins and oils. At the same time, products which employ these ingredients are designed to impart certain desirable properties such as shine, water resistance, transfer resistance, scratch resistance, color and a glazed appearance to a surface. Furthermore, when the surface is a keratinous substrate such as hair or skin, these products are made to impart cosmetic benefits such as conditioning, smoothing, color, or style or shape to hair.

Nevertheless, consumers continuously seek new products with improved performance and therefore, challenges still exist today in terms of optimizing or enhancing the performance of these ingredients in various products. Moreover, the formulation of waxes, polymers, resins and oils in various galenic forms such as sprays, foams, emulsions, gels, mousses, pastes and sticks may pose a challenge since some of these ingredients may not be easily introduced and/or dispersed into these galenic forms. In addition, the final formulas using these ingredients have to remain stable over time.

In the area of hair care, hair styling products which contain one or more of polymers can be used to impart shape or style to the hair and/or to help maintain a particular hair style. The goals of many hair styling compositions include to hold or fix the hair in a particular shape, to impart or increase volume of the hair, and/or to smooth the hair, e.g. to decrease or eliminate the appearance of frizz. However, the type and/or amounts of such polymers can pose a challenge with respect to optimizing the benefits that can be obtained from the polymers themselves. Thus, there still exists a need to improve how ingredients such as, polymers, resins and oils can be formulated into various galenic forms, and at the same time, optimize the benefits derived from these ingredients and enhance the performance of other ingredients.

Drawbacks associated with current products for styling the hair include that the product is often sticky or tacky and/or often produces a film that imparts a sticky or tacky feel, as well as produces undesirable flaking on surfaces, including hair, and styled hair that is stiff and/or "crunchy" (i.e. the film is hard and brittle resulting in a crunching feel or sound when the hair is touched), which is undesirable for most consumers. Current products for styling the hair typically include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film. These products also tend to exhibit problems with product spreadability, hair manageability, and low degree of humidity resistance which is particularly a problem in hot and humid countries.

It has now been discovered that by providing a composition comprising one or more latex polymers chosen from acrylate latex polymers and polyurethane latex polymers, a dispersion of particles of at least one silicone latex polymer, and optionally, a solvent, it is possible to form a film or coating on hair that has certain desirable properties, such as a clean, natural, and/or "invisible" feel, no flaking, and a lack of stickiness as well as provides hair styling benefits such as a natural look, curling or straightening, and styling hold to hair. In addition, while the general aim of hair styling or shaping products is to hold the hair in a certain shape, it was surprisingly and unexpectedly found that the association of the silicone latex polymer with the latex polymer resulted in product that not only held the hair in a certain configuration, but also provided to the hair a soft, smooth, and conditioned feel to the touch. Thus, the compositions of the invention were found to provide various degrees of styling hold to the hair and at the same time, a desirable texture and feel to the hair.

Moreover, compositions according to embodiments of the disclosure may be prepared that deliver a surprisingly broad range of hair styling benefits, such as, for example, from low to high style-hold as well as good curl-retention properties, for example by varying the weight ratio between different types of latex polymers that are chosen from acrylate latex polymers and polyurethane latex polymers, and/or between said latex polymers and the at least one silicone latex polymer, with or without additives.

BRIEF SUMMARY OF THE INVENTION

The present invention relates, in various embodiments, to hair styling compositions containing:
(a) one or more latex polymers selected from acrylate latex polymers, polyurethane latex polymers, and mixtures thereof;
(b) a dispersion of particles of at least one silicone latex polymer;
and optionally,
(c) a solvent;
wherein the weight ratio of the at least one silicone latex polymer (b) to the latex polymers (a) ranges from about 10:1 to about 1:10; and
wherein the composition produces a film having a Young's modulus ranging up about 1 GPa, and a strain, under stress at 10 MPa, of less than about 70%.

In further embodiments, methods of styling the hair are disclosed, said methods comprising applying compositions according to the disclosure to the hair. Such styling methods may comprise shaping, reshaping, positioning, repositioning, adding volume to, curling, or straightening the hair, in order to achieve a certain hair style or appearance.

DETAILED DESCRIPTION OF THE INVENTION

As used herein, the expression "at least one" means "one or more" and vice versa and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The term "comprising" (and its grammatical variations) as used herein is used in the inclusive sense of "having" or "including" and not in the exclusive sense of "consisting only of".

"Keratinous fiber" as used herein, includes, but is not limited to hair, such as hair on the human head and eyelashes.

As used herein, the terms "applying a composition onto keratin fibers" and "applying a composition onto hair" and variations of these phrases are intended to mean contacting the fibers or hair, with at least one of the compositions of the invention, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions of the present invention onto keratinous substrates such as hair; the term also refers to contacting said substrates with the compositions of the present invention.

"Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

The compositions and methods of the present invention can comprise, consist of, or consist essentially of the essential elements and limitations of the invention described herein, as well as any additional or optional ingredients, components, or limitations described herein or otherwise useful.

Unless otherwise indicated, percentages by weight of the latex polymers in the compositions of the present invention are presented on a dry weight basis (or as amounts of active material).

In one embodiment, the present invention is directed to hair styling compositions containing:
  (a) from about 0.25% to about 8% by weight of one or more latex polymers selected from acrylate latex polymers, polyurethane latex polymers, and mixtures thereof;
  (b) a dispersion of particles of at least one silicone latex polymer wherein the at least one silicone polymer is present in an amount of from about 1% to about 5% by weight;
  and optionally,
  (c) a solvent;
wherein the weight ratio of the at least one silicone latex polymer (b) to the latex polymers (a) ranges from about 5:1 to about 1:5; and
wherein the composition produces a film having a Young's modulus ranging up about 1 GPa, and a strain, under stress at 10 MPa, of less than about 70%;
all weights being based on the total weight of the composition; and
all weights based on a dry weight basis.

In certain embodiments, the latex polymers (a) may be selected from:
  (i) polymer A, having a Young's modulus ranging from about 0.1 MPa to about 10 MPa and a strain, under stress at 10 MPa, of at least about 1%; and
  (ii) polymer B, having a Young's modulus ranging from about 10 MPa to about 5 GPa and a strain, under stress at 10 MPa, of less than about 5%.

In an embodiment, the present invention is directed to hair styling compositions containing:
  (a) from about 0.25% to about 9% by weight of one or more latex polymers selected from a polycarbonate polyurethane, aliphatic polyurethane, aliphatic polyester polyurethane, polyurethane-34, polyurethane-48, Acrylates Copolymer, Polyacrylate-2 Crosspolymer, Acrylates/Hydroxyesters Acrylate Copolymer, Acrylate/Ethylhexyl Acrylate Copolymer, Styrene Acrylate Copolymer, Acrylate/VA Copolymer, Styrene/Acrylic copolymer, Styrene/Acrylates Copolymer, Styrene/Acrylates/Ammonium Methacrylate Copolymer and mixtures thereof;
  (b) a dispersion of particles of at least one silicone latex polymer wherein the at least one silicone polymer is present in an amount of from about 1% to about 10% by weight and is selected from a linear block silicone copolymer, a polymethylsiloxane resin, and mixtures thereof;
  and optionally,
  (c) a solvent;
wherein the latex polymers (a) are selected from:
  (i) polymer A, having a Young's modulus ranging from about 0.1 MPa to about 10 MPa and a strain, under stress at 10 MPa, of at least about 0.1%; and
  (ii) polymer B, having a Young's modulus ranging from about 10 MPa to about 5 GPa and a strain, under stress at 10 MPa, of less than about 5%; and
  (iii) mixtures thereof;
all weights being based on the total weight of the composition;
all weights based on a dry weight basis;
wherein the weight ratio of the at least one silicone latex polymer (b) to the latex polymers (a) ranges from about 3:1 to about 1:3; and
wherein the composition produces a film having a Young's modulus ranging up about 1 GPa, and a strain, under stress at 10 MPa, of less than about 70%.

In yet another embodiment, the present invention is directed to hair styling compositions containing:
  (a) from about 0.5 to about 2.5% by weight of one or more latex polymers selected from acrylate latex polymers, polyurethane latex polymers, and mixtures thereof;

(b) a dispersion of particles of at least one silicone latex polymer wherein the at least one silicone polymer is present in an amount of from about 0.5% to about 2.5% by weight;
and optionally,
(c) a solvent;
all weights being based on the total weight of the composition;
all weights based on a dry weight basis;
wherein the weight ratio of the at least one silicone latex polymer (b) to the latex polymers (a) ranges from about 3:1 to about 1:3; and
wherein the composition produces a film having a Young's modulus ranging up about 1 GPa, and a strain, under stress at 10 MPa, of less than about 70%.

In any one of the above embodiments, the latex polymers in (a) are in the form of particles dispersed in an aqueous dispersion medium.

In certain embodiments, the latex polymers (a) may be selected from:
(iii) polymer A, having a Young's modulus ranging from about 0.1 MPa to about 10 MPa and a strain, under stress at 10 MPa, of at least about 1%; and
(iv) polymer B, having a Young's modulus ranging from about 10 MPa to about 5 GPa and a strain, under stress at 10 MPa, of less than about 5%.

In some embodiments, the acrylate latex polymers may be selected from acrylates copolymer, Acrylates/ethylhexyl acrylate copolymer, and mixtures thereof.

In some embodiments, the polyurethane latex polymers may be selected from polyurethane-34.

In other embodiments, the silicone latex polymer may be selected from a linear block silicone copolymer which is in the form of particles dispersed in an aqueous dispersion medium and wherein the linear block silicone copolymer is divinyldimethicone/dimethicone copolymer and known under the tradename of HMW 2220 from the company Dow Corning.

In yet other embodiments, the silicone latex polymer may be selected from a polymethylsiloxane resin present in the aqueous emulsion medium with a solid content of about 43% by weight, based on the weight of the emulsion and available under the tradename of tradename BLUESIL BP 9878, commercially available from the company Bluestar Silicones.

In one embodiment, the present invention is directed to hair styling compositions containing:
(a) from about 0.25% to about 9% by weight of at least two latex polymers, independently selected from acrylate latex polymers and polyurethane latex polymers;
(b) a dispersion of particles of at least one silicone latex polymer wherein the at least one silicone polymer is present in an amount of from about 1% to about 10% by weight;
and optionally,
(c) a solvent;
wherein at least one of the latex polymers (a) is a film-forming polymer;
wherein the latex polymers are selected from:
(i) polymer A, having a Young's modulus ranging from about 0.1 MPa to about 10 MPa and a strain, under stress at 10 MPa, of at least about 1%; and
(ii) polymer B, having a Young's modulus ranging from about 10 MPa to about 5 GPa and a strain, under stress at 10 MPa, of less than about 5%;

all weights being based on the total weight of the composition;
all weights based on a dry weight basis;
wherein the weight ratio of the at least one silicone latex polymer (b) to the latex polymers (a) ranges from about 3:1 to about 1:3; and
wherein the composition produces a film having a Young's modulus ranging up about 1 GPa, and a strain, under stress at 10 MPa, of less than about 70%.

In one embodiment of the above-described composition comprising at least two latex polymers (a), polymer A is selected from polyurethane-34 and polymer B is selected from acrylates copolymer, Acrylates/ethylhexyl acrylate copolymer, and mixtures thereof.

In another embodiment of the above-described composition comprising at least two latex polymers (a), the at least one silicone latex polymer is selected from a linear block silicone copolymer which is in the form of particles dispersed in an aqueous dispersion medium and wherein the linear block silicone copolymer is divinyldimethicone/dimethicone copolymer and known under the tradename of HMW 2220 from the company Dow Corning.

In yet another embodiment of the above-described composition comprising at least two latex polymers (a), the silicone latex polymer may be selected from a polymethylsiloxane resin present in the aqueous emulsion medium with a solid content of about 43% by weight, based on the weight of the emulsion and available under the tradename of tradename BLUESIL BP 9878, commercially available from the company Bluestar Silicones.

In an embodiment of the above-described composition comprising at least two latex polymers (a), the composition comprises two latex polymers (a) wherein polymer A is polyurethane-4 and polymer B is acrylates copolymer or Acrylates/ethylhexyl acrylate copolymer.

In another embodiment of the above-described composition comprising at least two latex polymers (a), the composition comprises two latex polymers (a) wherein polymer A is polyurethane-4 and polymer B is acrylates copolymer and the weight ratio of the silicone latex polymer (b) to polymer A to polymer B is 1:1:1.

Stickiness, tackiness and flaking are undesirable properties generally attributed to the presence of the latex polymers in (a) above which are chosen from acrylate latex polymers and polyurethane latex polymers. With the association of the silicone latex polymers in (b) above with the latex polymers (a), it was surprisingly and unexpectedly discovered that the resulting compositions of the present invention had reduced or minimized stickiness or tackiness and did not produce flaking.

The compositions of the present invention can be applied onto various substrates to form a coating on the surface of a keratinous substrate such as hair. It was surprisingly and unexpectedly discovered that the coating on the surface of the substrate had no or minimal stickiness or tackiness.

The compositions of the present invention also imparted a clean and natural feel on the substrate. For example, when said compositions were applied onto a keratinous substrate such as hair, the coating formed on the hair did not undesirably stiffen the hair or cause the hair fibers or cause the fibers to be glued or stuck together. Instead, it was found that there was a natural feel to the hair, i.e., the coating was not heavy and/or thick.

Moreover, compositions of the present invention may easily be removed from the substrate by washing with water or with conventional cleansing agents.

Surprisingly and unexpectedly, it was also found that the compositions of the present invention provide anti-frizz properties and curl retention properties to hair. In addition, it was surprisingly and unexpectedly found that the compositions of the present invention can provide durable or long lasting styling benefits to hair.

Latex Polymers

According to various exemplary embodiments, the compositions of the present invention comprise one or more latex polymers chosen from acrylate latex polymers, polyurethane latex polymers, and mixtures thereof. The one or more latex polymers chosen from acrylate latex polymers, polyurethane latex polymers, and mixtures thereof of the present invention may also be referred to as "latex polymers (a)" in this application.

In various embodiments, the one or more latex polymers (a) of the present invention can be film-forming latex polymers or non film-forming latex polymers.

In various embodiments according to the disclosure, the latex polymers (a) are present, as polymeric active material (dry weight basis), in an amount ranging from about 0.1% to about 30% by weight, preferably about 0.2% to about 20% by weight, more preferably from about 0.25% to about 10% by weight, even more preferably from about 0.25% to about 8% by weight, including all ranges and subranges there between, based on the total weight of the composition.

In other various embodiments, the latex polymers (a) can be employed, as polymeric active material (dry weight basis), in an amount of about 0.1%, or about 0.5%, or about 1%, or about 1.5%, or about 2%, or about 2.5%, or about 3%, or about 3.5%, or about 4%, or about 4.5%, or about 5%, or about 5.5%, or about 6%, or about 6.5%, or about 7%, or about 7.5%, or about 8%, or about 8.5%, or about 9%, or about 9.5%, or about 10% by weight, based on the total weight of the composition.

In at least certain embodiments of the disclosure, the one or more latex polymers (a) are provided in the form of aqueous dispersions prior to formulating the compositions of the disclosure. In various embodiments, the aqueous dispersions may be obtained through an emulsion polymerization of monomers wherein the resulting latex polymers have a particle size lower than about 1 m. In at least one exemplary embodiment, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers are produced from condensation reactions between monomers and subsequently dispersed in an aqueous medium.

Thus, the latex polymers (a) may, in various exemplary embodiments, exist as dispersed polymer particles in a dispersion medium, such as an aqueous dispersion medium. The latex polymers may, in certain embodiments, each be dispersed in independent dispersion media. In yet further embodiments, the latex polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3- butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

In at least one embodiment, the solvent of the dispersion medium consists of water. In other embodiments, the solvent of the dispersion medium consists of water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the disclosure, the latex polymer (a) particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In at least certain exemplary embodiments, latex polymer (a) particles according to the disclosure may have an average diameter ranging up to about 1000 nm, such as from about 50 nm to about 800 nm, or from about 100 nm to about 500 nm. Such particle sizes may be measured with a laser granulometer (e.g. Brookhaven BI90).

In various embodiments, the latex polymers (a) may, independently, be neutralized, partially neutralized, or unneutralized. In exemplary embodiments where the latex polymers are neutralized or partially neutralized, the particle size may be, for example, greater than about 800 nm. In at least certain embodiments, the particulate form of the latex polymers is retained in the dispersion medium.

In further embodiments, the latex polymers (a) may be chosen from uncharged and charged latex polymers. Thus, the latex polymers (a) may, according to various exemplary embodiments, be chosen from nonionic latex polymers, cationic latex polymers, and anionic latex polymers.

As non-limiting examples of latex polymers (a) that may be used, mention may be made, independently, of acrylate latex polymers and polyurethane latex polymers.

By way of non-limiting example only, the latex polymers (a) may be chosen from acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl(meth)acrylic, such as, for example, methyl(meth)acrylic, ethyl(meth)acrylic, propyl(meth)acrylic, isopropyl(meth)acrylic, butyl(meth)acrylic, tert-butyl(meth)acrylic, pentyl(meth)acrylic, isopentyl(meth)acrylic, neopentyl(meth)acrylic, hexyl(meth)acrylic, isohexyl(meth)acrylic, 2-ethylhexyl(meth)acrylic, cyclohexyl(meth)acrylic, isohexyl(meth)acrylic, heptyl(meth)acrylic, isoheptyl(meth)acrylic, octyl(meth) acrylic, isooctyl(meth)acrylic, as well as combinations of any of the above.

The esters of (meth)acrylic monomers may be, by way of non-limiting example, C1-C8 alkyl(meth)acrylates such as methyl(meth)acrylate, ethyl(meth)acrylate, propyl(meth) acrylate, isopropyl(meth)acrylate, butyl(meth)acrylate, tert-butyl(meth)acrylate, pentyl(meth)acrylate, isopentyl(meth) acrylate, neopentyl(meth)acrylate, hexyl(meth)acrylate, isohexyl(meth)acrylate, 2-ethylhexyl(meth)acrylate, cyclohexyl(meth)acrylate, isohexyl(meth)acrylate, heptyl(meth) acrylate, isoheptyl(meth)acrylate, octyl(meth)acrylate, isooctyl(meth)acrylate, allyl(meth)acrylate, and combinations thereof. Additional and non-limiting examples include C1-C8 alkoxy(meth)acrylates, such as methoxy(meth)acrylate, ethoxy(meth)acrylate, propyl oxide(meth)acrylate, isopropyl oxide(meth)acrylate, butyl oxide(meth)acrylate, tert-butyl oxide(meth)acrylate, pentyl oxide(meth)acrylate, isopentyl oxide(meth)acrylate, neopentyl oxide(meth)acrylate. The esters may be, by way of non-limiting example, C2-C6 hydroxy alkyl(meth)acrylates, such as hydroxy ethyl (meth)acrylate, 2-hydroxypropyl(meth)acrylate, glycidyl (meth)acrylate, ethylene glycol di(meth)acrylate, polyethylene glycol mono(meth)acrylate, 1,4-butane diol di(meth) acrylate, 1,6,hexane diol di(meth)acrylate, and any combination thereof. The esters may be, by way of non-limiting example, aryl(meth)acrylates such as benzyl(meth) acrylate, phenyl(meth)acrylate, and any combination thereof. The esters can further contain amino groups such as aminoethyl(meth)acrylate, N,N-dimethylaminoethyl(meth) acrylate, N,N-dimethylaminopropyl(meth)acrylate, N,N-dimethylaminodimethylpropyl(meth)acrylate, N,N-diethyleaminoethyl(meth)acrylate, and N,N,N-trimethylaminoethyl(meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12) alkyl(meth) acrylates such as N-ethyl(meth)acrylamide, N-t-butyl(meth) acrylamide, N-t-octyl(meth)acrylamide, N-methylol(meth) acrylamide and N-diacetone(meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

In at least certain, non-limiting exemplary embodiments, acrylate latex polymers may be chosen from aqueous dispersions of Methacrylic Acid/Ethyl Acrylate copolymer (INCI: Acrylates Copolymer, such as LUVIFLEX® SOFT by BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI: Polyacrylate-2 Crosspolymer, such as FIXATE SUPERHOLD™ by Lubrizol), Styrene/Acrylic copolymer (such as NEOCRYL® A-1120, DSM), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as Daitosol 5000SJ, Daito Kasei Kogyo), Acrylic/Acrylates Copolymer (INCI name: Acrylates Copolymer, such as DAITOSOL 5000AD, Daito Kasei Kogyo), Vinyl Acetate Acrylic Ester Copolymer (INCI name: Acrylates/VA Copolymer, such as VINYSOL 2140, Daido Chemical), Acrylates Copolymers, such as those known under the tradename ACULYN™ 33 (Dow Chemical), under the tradename LUVIMER® MAE (BASF), or under the tradename BALANCE CR (AKZO NOBEL), and Acrylates/Hydroxyesters Acrylates Copolymer, known under the tradename ACUDYNE 180 POLYMER (Dow Chemical), Styrene/Acrylates Copolymer, known under the tradename JONCRYL 77 from BASF, Styrene/Acrylates/Ammonium Methacrylate Copolymer, known under the tradename SYNTRAN PC5620 CG from Interpolymer, and mixtures thereof.

In yet further exemplary and non-limiting embodiments, the film-forming latex polymers may be chosen from polyurethane latex polymers, such as aqueous polyurethane dispersions comprising the reaction products of (i), (ii), and/or (iii), defined below.

Reaction product (i) may be any prepolymer according to the formula:

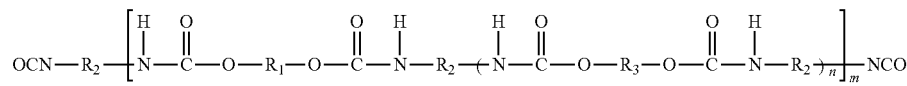

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecanedioic, 1,3-cyclohexanedicarboxylic, 1,4-cyclohexanedicarboxylic, 2,5-norboranedicarboxylic, diglycolic, thiodipropionic, 2,5-naphthalenedicarboxylic, 2,6-naphthalenedicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythioether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexanediol. Polyacetals useful according to various non-limiting embodiments of the disclosure can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula $R_2(NCO)_2$, in which $R_2$ represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanatomethyl-3,5,5-trimethylcyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxycyclohexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylolbutanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

H2N—R4-NH2 wherein R4 is chosen from alkylene or alkylene oxide radicals, said radicals not being substituted with ionic or potentially ionic groups.

Reaction product (ii) may optionally be chosen from alkylene diamines, such as hydrazine, ethylenediamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophoronediamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

H2N—R5-NH2 wherein R5 is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, R5 represents an alkylene radical substituted with sulphonic acid or sulphonate groups. By way of example only, the compound is chosen from sodium salts of N-(2-aminoethyl)-2-aminoethanesulphonic acid.

By way of non-limiting example, such latexes include, but are not limited to, aqueous polyurethane dispersions comprising a reaction product of a prepolymer such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), polycarbonate polyurethane, aliphatic polyurethane and aliphatic polyester polyurethane (such as the NEOREZ® series, DSM, such as NEOREZ® R989 (INCI name: Polycarbamyl Polyglycol Ester), and NEOREZ® R-2202).

In certain embodiments, the latex polymers (a) of the present invention chosen from acrylate latex polymers or polyurethane latex polymers, or mixtures thereof are film-forming latex polymers.

In certain other embodiments, the latex polymers (a) of the present invention are non film-forming latex polymers.

In other embodiments, the latex polymers (a) of the present invention comprise at least two latex polymers selected from acrylate latex polymer and polyurethane latex polymers.

In some embodiments, at least one of the at least two latex polymers (a) selected from acrylate latex polymers and a polyurethane latex polymer is a film-forming latex polymer.

In other embodiments, the latex polymers (a) in the compositions of the present invention comprise two latex polymers selected from acrylate latex polymers or from polyurethane latex polymers. In some embodiments, one of the two latex polymers selected from acrylate latex polymers or from polyurethane latex polymers is a film-forming latex polymer. In other embodiments, both of the two latex polymers are film-forming latex polymers.

In various embodiments, when the first latex polymer is chosen from an acrylate polymer, the second latex polymer is chosen from a polyurethane polymer; and when the first latex polymer is chosen from a polyurethane polymer, the second latex polymer is chosen from an acrylate polymer.

In some embodiments, the acrylate latex polymers and the polyurethane latex polymers are present in the compositions of the present invention in a weight ratio of about 10:1 to about 1:10.

In various embodiments, when the one or more latex polymers in the compositions of the present invention comprise at least two latex polymers chosen from acrylate latex polymers and polyurethane latex polymers, these latex polymers may be identified as polymer A and polymer B. Compositions according to certain embodiments may comprise at least one polymer A and at least one polymer B.

In various embodiments, polymer A may be chosen from latex polymers having a Young's modulus ranging from about 0.1 MPa to about 10 MPa and a strain, under stress at 10 MPa, of at least about 0.1%; and polymer B may be chosen from latex polymers having a Young's modulus ranging from about 10 MPa to about 5 GPa and a strain, under stress at 10 MPa, of less than about 5%. In at least certain embodiments, then polymer A may have a glass transition temperature (Tg) ranging from about −90° C. to about 40° C., and polymer B may have a glass transition temperature (Tg) ranging from about 40° C. to about 200° C. In at least certain other embodiments, the weight ratio of polymer A to polymer B in the compositions of the disclosure is from about 1:10 to about 1:1, from about 3:1 to about 10:1, or from about 5:1 to about 10:1.

In some embodiments, Polymers A and B may be chosen from acrylate latex polymers and polyurethane latex polymers, with the proviso that when polymer A is chosen from an acrylate latex polymer, polymer B is chosen from a polyurethane latex polymer; and when polymer A is chosen from a polyurethane latex polymer, polymer B is chosen from an acrylate latex polymer.

In at least certain exemplary and non-limiting embodiments, latex polymers A and B may be chosen such that polymer A comprises at least one latex polymer that is a relatively soft, flexible latex polymer, and polymer B comprises at least one latex polymer that is a relatively hard, brittle polymer, although such characteristics are not required.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at ambient temperature or below, or in other words, will only form a film at temperatures above ambient. For purposes of this disclosure, ambient temperature is taken as being below 40° C. such as in the range of 15° C. to 30° C.

By "one or more latex polymers," it is contemplated that at least one latex polymer chosen from acrylate latex polymers, polyurethane latex polymers, and mixtures thereof may be present in the compositions of the invention. Thus, for example, in various embodiments, when more than one latex polymer chosen from acrylate latex polymers, polyurethane latex polymers, and mixtures thereof are employed, the composition may comprise polymers A and/or B, with the proviso that when both polymers A and B are present, the first latex polymer, polymer A, is chosen from acrylate latex polymers, the second latex polymer, polymer B, is chosen from polyurethane latex polymers; and when the first latex polymer, polymer A, is chosen from polyurethane latex polymers, the second latex polymer, polymer B, is chosen from acrylate latex polymers.

In further embodiments, the composition comprises exactly two latex polymers (a) wherein at least one latex polymer is a film-forming latex polymer. According to additional embodiments, the composition comprises exactly two film-forming latex polymers.

In at least certain embodiments, film-forming latex polymers may be chosen from polyacrylic latex, polyacrylate latex, polystyrene latex, polyester latex, polyamide latex, polyurea latex, polyurethrane latex, epoxy resin latex, and their copolymers.

In various embodiments according to the disclosure, it may be possible to choose a polymer that comprises both acrylate and polyurethane parts at the molecular level.

Silicone Latex Polymer

The compositions of the present invention comprise a dispersion of particles of at least one silicone latex polymer.

The at least one silicone latex polymer according to the invention is chosen from a polymethylsiloxane resin, a linear block copolymer (or linear block silicone copolymer), and mixtures thereof.

Preferably, the at least one silicone latex polymer is nonionic.

In certain embodiments, the at least one silicone latex polymer of the present invention is not prepared from acrylic acid monomers or acrylate ester monomers.

In other embodiments, the at least one silicone latex polymer of the present invention is nonionic and is not prepared from acrylic acid monomers or acrylate ester monomers.

The at least one silicone latex polymer according to the invention may be chosen from non-film-forming silicone latex polymers and film-forming silicone latex polymers.

The at least one silicone latex polymer can be present in the composition of the present invention in an amount, as polymeric active materials (dry weight basis), ranging from 0.1 percent to 30 percent by weight, preferably from 0.5 percent to 20 percent by weight, more preferably from 1 percent to 10 percent by weight, and even more preferably from 1 percent to 5 percent by weight, including all ranges and subranges therebetween, based on the total weight of the composition.

In various embodiments, the at least one silicone latex polymer can be employed in the composition of the present invention, as polymeric active material (dry weight basis), in an amount of about 0.1%, or about 0.5%, or about 1%, or about 1.5%, or about 2%, or about 2.5%, or about 3%, or about 3.5%, or about 4%, or about 4.5%, or about 5%, or about 5.5%, or about 6%, or about 6.5%, or about 7%, or about 7.5%, or about 8%, or about 8.5%, or about 9%, or about 9.5%, or about 10% by weight, based on the total weight of the composition.

Polymethylsiloxane Resin

The polymethylsiloxane resin of the present invention is preferably in the form of an emulsion.

In certain embodiments, the polymethylsiloxane resin is in an aqueous emulsion medium and is present in the emulsion with a solid content of about 43% by weight, based on the weight of the emulsion. An example of a polymethylsiloxane resin emulsion is the material known by the tradename BLUESIL BP 9878, commercially available from the company Bluestar Silicones; such a material employs a nonionic emulsifier.

Linear Block Silicone Copolymer

The linear block silicone copolymer used in the composition according to the invention is an uncrosslinked block copolymer, obtained by chain extension and not by crosslinking.

The term "block copolymer" (or "sequential copolymer") denotes a polymer comprising at least two distinct blocks (sequences). Each block of the polymer results from one type of monomer or from several types of different monomers. This means that each block can be composed of a homopolymer or of a copolymer, it being possible for this copolymer constituting the block to be in its turn a random or alternating copolymer.

The linear block silicone copolymer used in the composition according to the invention preferably comprises at least two distinct silicone blocks, each block of the polymer resulting from one type of silicone monomer or from several types of different silicone monomers, such as mentioned below.

It should also be noted that the copolymer is "linear"; in other words, the structure of the polymer is neither branched nor star-branched nor grafted.

The linear block silicone copolymer is advantageously provided in the form of particles in dispersion in an aqueous medium.

The aqueous dispersion of block copolymer particles is a silicone-in-water (Sil/W) emulsion, the oily globules of which are composed of a silicone of high viscosity, so that these globules appear to form as "soft particles".

The size of the linear block silicone copolymer particles can vary widely. Preferably, in the present patent application, the linear block silicone copolymer particles generally exhibit a number-average size of less than or equal to 2 microns and preferably of less than or equal to 1 micron.

The aqueous dispersions of linear block silicone copolymer particles used in the composition according to the invention can be chosen in particular from those described in the document EP-A-874 017, the teaching of which is incorporated here by reference. According to this document, it is possible in particular to obtain the silicone copolymers constituting these particles by a chain extension reaction in the presence of a catalyst, starting from at least:

(a) one polysiloxane (i) having at least one reactive group and preferably one or two reactive groups per molecule; and (b) one organosilicone compound (ii) which reacts with the polysiloxane (i) by a chain extension reaction.

In particular, the polysiloxane (i) is chosen from the compounds of formula (I):

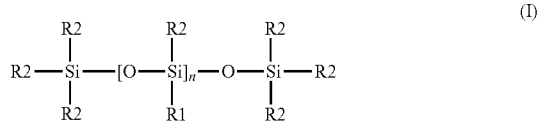

in which R1 and R2 represent, independently of one another, a hydrocarbon group having from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" is understood to mean any group capable of reacting with the organosilicone compound (ii) to form a block copolymer. Mention may be made, as reactive groups, of hydrogen; aliphatically unsaturated groups, and in particular vinyl, allyl or hexenyl groups; the hydroxyl group; alkoxy groups, such as methoxy, ethoxy or propoxy groups; alkoxy-alkoxy groups; the acetoxy group; amino groups, and mixtures thereof. Preferably, more than 90 percent and better still more than 98 percent of reactive groups are at the chain end, that is to say that the R2 radicals generally constitute more than 90 percent and even 98 percent of the reactive groups. n can in particular be an integer ranging from 2 to 100, preferably from 10 to 30 and better still from 15 to 25.

The polysiloxanes of formula (I) are linear polymers, that is to say comprising few branchings and generally less than 2 mole percent of siloxane units. Furthermore, the R1 and R2 groups can optionally be substituted by amino groups, epoxy groups or sulfur-comprising, silicon-comprising or oxygen-comprising groups.

Preferably, at least 80 percent of the R1 groups are alkyl groups and better still methyl groups.

Preferably, the reactive group R2 at the chain end is an aliphatically unsaturated group and in particular a vinyl group.

Mention may in particular be made, as polysiloxanes (i), of dimethylvinylsiloxy-polydimethylsiloxane, a compound of formula (I) in which the R1 radicals are methyl radicals and the R2 radicals at the chain end are vinyl radicals while the other two R2 radicals are methyl radicals.

The organosilicone compound (ii) can be chosen from polysiloxanes of formula (I) or compounds acting as chain-extending agent. If it is a compound of formula (I), the polysiloxane (i) will comprise a first reactive group and the organosilicone compound (ii) will comprise a second reactive group which will react with the first. If it is a chain-extending agent, it can be a silane, a siloxane (disiloxane or trisiloxane) or a silazane. Preferably, the organosilicone compound (ii) is a liquid organohydropolysiloxane of formula (II):

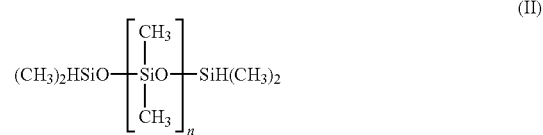

where n is an integer greater than 1 and preferably greater than 10, for example ranging from 2 to 100, preferably from 10 to 30 and better still from 15 to 25. According to a specific embodiment of the invention, n is equal to 20.

The linear block silicone copolymers used according to the invention are advantageously devoid of oxyalkylene group(s), in particular devoid of oxyethylene and/or oxypropylene group(s).

The catalyst of the reaction between the polysiloxane and the organosilicone compound can be chosen from metals and in particular from platinum, rhodium, tin, titanium, copper and lead. It is preferably platinum or rhodium.

The dispersion of linear block silicone copolymer particles used in the composition according to the invention can in particular be obtained, for example, by mixing (a) water, (b) at least one emulsifier, (c) the polysiloxane (i), (d) the organosilicone compound (ii) and (e) a catalyst. Preferably, one of the constituents (c), (d) or (e) is added last to the mixture, in order for the chain-extending reaction to begin only in the dispersion.

Mention may be made, as emulsifiers capable of being used in the preparation process described above in order to obtain the aqueous dispersion of particles, of non-ionic or ionic (anionic, cationic or amphoteric) emulsifiers. They are preferably non-ionic emulsifiers which can be chosen from polyalkylene glycol ethers of fatty alcohol comprising from 8 to 30 carbon atoms and preferably from 10 to 22 carbon atoms; polyoxyalkylenated and in particular polyoxyethylenated sorbitan alkyl esters, where the alkyl radical comprises from 8 to 30 carbon atoms and preferably from 10 to 22 carbon atoms; polyoxyalkylenated and in particular polyoxyethylenated alkyl esters, where the alkyl radical comprises from 8 to 30 carbon atoms and preferably from 10 to 22 carbon atoms; polyethylene glycols; polypropylene glycols; diethylene glycols; and mixtures thereof. The amount of emulsifier(s) is generally from 1 percent to 30 percent by weight, including all ranges and subranges therebetween, based on the total weight of the reaction mixture.

The emulsifier used to obtain the aqueous dispersion of particles is preferably chosen from polyethylene glycol ethers of fatty alcohols and mixtures thereof and in particular polyethylene glycol ethers of alcohols comprising 12 or 13 carbon atoms and from 2 to 100 oxyethylene units and preferably from 3 to 50 oxyethylene units, and mixtures thereof. Mention may be made, for example, of $C_{12}$-$C_{13}$ Pareth-3, $C_{12}$-$C_{13}$ Pareth-23 and mixtures thereof.

According to a specific embodiment of the invention, the dispersion of silicone copolymer particles is obtained from dimethylvinylsiloxy-polydimethylsiloxane (or divinyldimethicone), as compound (i), and from the compound of formula (II) with preferably n=20, as compound (ii), preferably in the presence of a catalyst of platinum type, and the dispersion of particles is preferably obtained in the presence of $C_{12}$-$C_{13}$ Pareth-3 and $C_{12}$-$C_{13}$ Pareth-23, as emulsifiers.

Use may in particular be made, as dispersion of silicone copolymer particles, of the product sold under the name HMW 2220 by Dow Corning (CTFA name: divinyldimethicone/dimethicone copolymer/$C_{12}$-$C_{13}$ Pareth-3/$C_{12}$-$C_{13}$ Pareth-23), which is a 60 percent aqueous dispersion of divinyldimethicone/dimethicone copolymer and comprising $C_{12}$-$C_{13}$ Pareth-3 and $C_{12}$-$C_{13}$ Pareth-23, said dispersion comprising approximately 60 percent by weight of copolymer, 2.8 percent by weight of $C_{12}$-$C_{13}$ Pareth-23, 2 percent by weight of $C_{12}$-$C_{13}$ Pareth-3 and 0.31 percent by weight of preservatives, the remainder to 100 percent being water.

Solvent

The solvent (also designated as "additional solvent") that may further comprise the compositions of the present invention is a separate component from the solvent/medium/carrier comprising the dispersion comprising the film forming latex polymers or the dispersion comprising the at least one silicone latex polymer of the present invention.

The additional solvent of the present invention may be selected from water, at least one organic solvent, and mixtures thereof.

Water can be employed in the amount of about 95%, 90%, 80%, 70%, 60%, 50%, 40%, 30%, 20%, 10%, 5% by weight or less, relative the total weight of the compositions. Additionally, water can be present in the compositions of the present invention in the amount of from about 20% to about 95% by weight, or from about 50% to about 90% by weight, or from about 60% to about 80% by weight, including all ranges and subranges therebetween, based on the total weight of the composition of the present invention.

In other embodiments, water can be present in the compositions of the present invention in the amount of at least about 95%, 90%, 80%, 70%, 60%, 50%, 40%, 30%, 20%, 10%, 5% by weight or less, relative to the total weight of the compositions.

Suitable organic solvents may be chosen from volatile and nonvolatile organic solvents.

Suitable organic solvents are typically C1-04 lower alcohols, glycols, polyols, polyol ethers, hydrocarbons, and oils. Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW ϵ-series and DOW P-series. One preferred glycol ether for use in the present invention is dipropylene glycol n-butyl ether, known under the tradename of DOWANOL DPnB.

Suitable organic solvents also include synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, isoparaffins, isododecanes, aromatic hydrocarbons, polybutene, hydrogenated polyisobutene, hydrogenated polydecene, polydecene, squalene, petrolatum and isoparaffins, silicone oils, fluoro oils and mixtures, thereof.

The term "hydrocarbon-based oil" or "hydrocarbon oil" refers to oil mainly containing hydrogen and carbon atoms and possibly oxygen, nitrogen, sulfur and/or phosphorus atoms. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Other representative examples of silicone oils that may be useful in the present invention include volatile silicone oils such as linear or cyclic silicone oils, especially those with a viscosity ÿ centistokes (8×10-6 m 2/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluro oils such as nonafluoromethoxybutane and perfluoro-methylcyclopentane.

The amount of the organic solvent/compound present in the compositions of the present invention can range from about 0.5% to about 95%, or from about 0.5% to about 80%, or from about 0.5% to about 60%, or from about 0.5% to about 40%, or from about 0.5% to about 30%, or from about 0.5% to about 20%, and in some embodiments, from about 0.5% to about 15%, by weight, or preferably from about 1% to about 10%, by weight, or more preferably from about 1.5% to about 8%, by weight, or from about 2% to about 6%, by weight, including all ranges and subranges there-be-tween, based on the total weight of the composition.

In some embodiments, the amount of the organic solvent/compound present in the compositions of the present invention is at about 2%, about 2.5%, about 3%, about 3.5%, about 4%, about 4.5%, about 5%, about 5.5% or about 6% by weight, including all ranges and subranges there-be-tween, based on the total weight of the composition.

In some other embodiments, the amount of the organic solvent/compound present in the compositions of the present invention is at about 95%, about 90%, about 85%, about 80%, about 75%, about 70%, about 65%, about 60% or about 55% by weight, including all ranges and subranges there-between, based on the total weight of the composition.

In certain embodiments, the additional solvent in the compositions of the present invention comprise both water and organic solvents/compounds selected from volatile organic solvents, non-volatile organic solvents, and mixtures thereof.

Preferred examples of organic solvents/compounds include volatile organic solvents such as C2 to C4 monoalcohols, such as ethanol, isopropyl alcohol, butanol, polyols such as C2-C6 glycols e.g., propylene glycol, butylene glycol, pentylene glycol, hexylene glycol, glycerol, isododecane, volatile polyol ethers, volatile glycol ethers, acetone, propylene carbonate, benzyl alcohol, and mixtures thereof. In certain embodiments, the amount of volatile organic solvent/compound does not exceed 55% by weight, relative to the weight of the composition of the present invention.

In other certain embodiments, it is preferred that the amount of volatile organic solvent/compound does not exceed 20% by weight, relative to the weight of the composition of the present invention.

In yet other certain embodiments, it is preferred that the amount of volatile organic solvent/compound does not exceed 10% by weight, relative to the weight of the composition of the present invention.

In preferred embodiments, the amount of volatile organic solvent/compound does not exceed 6% by weight, relative to the weight of the composition of the present invention.

Other preferred examples of organic solvents/compounds include nonvolatile organic solvents such as hydrocarbons such as straight chain hydrocarbons, nonvolatile silicone oils, mineral oil, polybutene, hydrogenated polyisobutene, hydrogenated polydecene, polydecene, squalene, petrolatum, isoparaffins, nonvolatile glycol ethers, and mixtures, thereof.

In certain embodiments, it is preferred that the amount of nonvolatile organic solvent/compound does not exceed 40% by weight, relative to the weight of the composition of the present invention.

In other certain embodiments, it is preferred that the amount of nonvolatile organic solvent/compound does not exceed 20% by weight, relative to the weight of the composition of the present invention.

In yet other certain embodiments, it is preferred that the amount of nonvolatile organic solvent/compound does not exceed 10% by weight, relative to the weight of the composition of the present invention.

In preferred embodiments of the present invention, the at least one organic solvent is chosen from ethanol, glycol ether, for example, dipropylene glycol n-butyl ether, known under the tradename of DOWANOL DPnB, isododecane, mineral oil, propylene glycol, pentylene glycol, hexylene glycol, glycerol, and mixtures thereof.

In certain embodiments of the present invention, the at least one organic solvent is chosen from ethanol.

In yet some other embodiments, water and/or the at least one organic solvent are not added as separate ingredients, by themselves, into the compositions of the present invention, such that water and/or the at least one organic solvent are present in the compositions of the present invention when they accompany one or more ingredients of a raw material, for example, the film-forming latex polymers or the silicone latex polymer, into the compositions of the present invention.

Methods of Making

The compositions of the invention may, according to at least certain exemplary embodiments, be obtained by means of a process comprising at least the following steps, although any process which produces the composition as described herein is contemplated to be within the scope of the disclosure.

The compositions of the present invention may be obtained by means of a process comprising at least the steps as follow:

A. combining:
 (a) one or more latex polymers selected from acrylate latex polymers, polyurethane latex polymers, and mixtures thereof;
 (b) a dispersion of particles of at least one silicone latex polymer;
 and optionally,
 (c) a solvent;
wherein the weight ratio of the at least one silicone latex polymer (b) to the latex polymers (a) ranges from about 10:1 to about 1:10; and B. mixing the components in (A) in order to form the hair styling composition; and wherein the composition produces a film having a Young's modulus ranging up about 1 GPa, and a strain, under stress at 10 MPa, of less than about 70%.

In certain embodiments, the latex polymers (a) are selected from:
 (i) polymer A, having a Young's modulus ranging from about 0.1 MPa to about 10 MPa and a strain, under stress at 10 MPa, of at least about 1%; and
 (ii) polymer B, having a Young's modulus ranging from about 10 MPa to about 5 GPa and a strain, under stress at 10 MPa, of less than about 5%.

Furthermore, in accordance with the process above, other ingredients, such as active ingredients, polymers other than latex polymers (a), and/or silicone latex polymer (b) and other additional ingredients as described above may be added during the preparation of the dispersion.

In an embodiment, the latex polymers (a) and/or silicone latex polymer (b) are preferably prepared in a dispersion in an aqueous and/or water-soluble continuous phase. Such a dispersion may also be described as an oil-in-water emulsion or an oil-in-water dispersion or an aqueous dispersion.

The aqueous and/or water-soluble continuous phase that is suitable for use in the dispersions comprising the latex polymers (a) and/or the silicone latex polymer (b) of the invention preferably comprises water such as demineralized water or a combination of water and a water-soluble solvent.

Among the water-soluble solvents that may be used in the dispersions in accordance with the invention, mention may be made especially of monoalcohols containing from 3+ carbon atoms, glycols, glycol ethers, and polyols, for instance glycerol, ethylene glycol, propylene glycol, butylene glycol, caprylyl glycol, hexylene glycol, dipropylene glycol, diethylene glycol, xylitol, sorbitol, mannitol, maltitol, and polyethylene glycol or mixtures thereof, C3 and C4 ketones, and C2-C4 aldehydes and mixtures thereof.

For the purposes of the present invention, the term "water-soluble solvent" is intended to denote a compound that is liquid at room temperature and water-miscible (miscibility in water of greater than 50% by weight at 25° C. and at atmospheric pressure).

According to yet another exemplary embodiment, the dispersions may comprise demineralized or deionized water as the continuous aqueous phase.

Compositions

As described herein, exemplary compositions according to the disclosure may comprise latex polymers chosen from acrylate latex and polyurethane latex polymers, a dispersion of particles of at least one silicone latex polymer; and optionally, a solvent; wherein the weight ratio of the at least one silicone latex polymer (b) to the latex polymers (a) ranges from about 10:1 to about 1:10; and wherein the composition produces a film having a Young's modulus ranging up about 1 GPa, and a strain, under stress at 10 MPa, of less than about 70%.

In some embodiments, the latex polymers (a) are selected from: polymer A, having a Young's modulus ranging from about 0.1 MPa to about 10 MPa and a strain, under stress at 10 MPa, of at least about 0.1%; and polymer B, having a Young's modulus ranging from about 10 MPa to about 5 GPa and a strain, under stress at 10 MPa, of less than about 5%.

The latex particles in this invention have an average diameter of from about 50 nm to about 800 nm, preferably from about 100 nm to about 500 nm. The latex polymers in the composition of the present invention must retain their particulate form in solution, i.e., the latex solution cannot be clear. In one embodiment, if the composition contains alcohols, the latex polymers are in particulate form upon removal of the alcohols.

In certain embodiments, the latex polymer is present in an amount ranging from about 0.25% to about 10% by weight, such as about 0.25% to about 9% by weight, such as about 0.25% to about 8% by weight, such as about 0.5% to about 5% by weight, or about 1% to about 5% by weight, based on the total weight of the composition, including all ranges and subranges there between.

In certain embodiments, when more than one latex polymer is employed, that is, at least two latex polymers selected from acrylate latex polymers and polyurethane latex polymers, are employed, the latex polymers are present in a combined amount ranging from about 0.1% to about 30% by weight, such as about 0.1% to about 25% by weight, such as about 0.2% to about 20% by weight, such as about 0.2% to about 15% by weight, such as about 0.25% to about 10% by weight, such as about 0.25% to about 8% by weight, such as about 0.5% to about 5% by weight, such as about 1% to about 3% by weight, or such as below about 30% by weight, or such as below about 20% by weight, or such as below about 10% by weight, based on the total weight of the composition, including all ranges and subranges there between. By way of non-limiting example, the combined amount of latex polymers may be about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight, based on the total weight of the composition.

In at least one exemplary embodiment, the combined amount of latex polymers is less than about 10% by weight, such as less than about 5% by weight, based on the total weight of the composition.

According to various embodiments of the disclosure, the weight ratio of the at least two latex polymers, e.g. polymer A to polymer B, may range from about 10:1 to about 1:10, such as about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2, including all ranges and subranges there between.

According to other embodiments of the disclosure, the weight ratio of the at least two latex polymers, e.g. polymer A to polymer B, may range from about 5:1 to about 1:3, or from about 3:1 to about 1:6, including all ranges and subranges there between.

According to various embodiments of the disclosure, the weight ratio of polymer A to polymer B is about 10:1, about 9:1, about 8:1, about 7:1, about 6:1, about 5:1, 4:1, about 3:1, about 2:1, about 1.85:1, about 1:1, about 1:2, about 1:3, about 1:4, about 1:5, about 1:5.6, about 1:6, about 1:7, about 1:8, about 1:9, or about 1:10.

In at least certain exemplary and non-limiting embodiments wherein the latex polymers in the composition of the present invention comprise acrylate latex polymers and polyurethane latex polymers, when polymer A is chosen from latex polymers having a Young's modulus ranging from about 0.1 MPa to about 10 MPa and a strain, under stress at 10 MPa, of at least about 0.1%, and polymer B is chosen from latex polymers having a Young's modulus ranging from about 10 MPa to about 5 GPa and a strain, under stress at 10 MPa, of less than about 5%, different weight ratios of polymer A to polymer B may be chosen to correspond to different hair styling applications. By way of example only, a weight ratio of polymer A to polymer B ranging from about 1:10 to about 1:1 may, in some embodiments, provide a high level of style hold; a weight ratio of polymer A to polymer B ranging from about 5:1 to about 10:1 may, in some embodiments, provide a medium to high level of style hold; and a weight ratio of polymer A to polymer B ranging from about 3:1 to about 10:1 may, in some embodiments, provide a light to medium level of style hold.

In at least certain exemplary and non-limiting embodiments, when polymer A is chosen from polyurethane latex polymers having a Young's modulus ranging from about 0.1 MPa to about 10 MPa and a strain, under stress at 10 MPa, of at least about 0.1%, and polymer B is chosen from acrylate latex polymers having a Young's modulus ranging from about 10 MPa to about 5 GPa and a strain, under stress at 10 MPa, of less than about 5%, different weight ratios of polymer A to polymer B may range from about 10:1 to about 1:10, such as about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2, including all ranges and subranges there between.

According to other embodiments of the disclosure, the weight ratio of the at least two latex polymers, that is, polymer A selected from polyurethane latex polymer to polymer B selected from acrylate latex polymer, is at about 1:3, or about 3:1, or about 1:2, or about 2:1, or about 1:1.

In certain embodiments, the at least one silicone latex polymer is present in an amount, as polymeric active material, ranging from about 0.25% to about 8% by weight, such as about 0.25% to about 7.5% by weight, such as about 0.5% to about 7% by weight, such as about 1% to about 5% by weight, or about 1% to about 3% by weight, based on the total weight of the composition, including all ranges and subranges there between.

According to various embodiments of the disclosure, the weight ratio of the at least one silicone latex polymer to the one or more latex polymer may range from about 10:1 to about 1:10, such as about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2, including all ranges and subranges there between.

According to some embodiments of the disclosure, the weight ratio of the at least one silicone latex polymer to the one or more latex polymer may range from about 5:1 to about 1:3, preferably, from about 3:1 to about 1:3, including all ranges and subranges there between.

According to various embodiments of the disclosure, the weight ratio of the at least one silicone latex polymer to the one or more latex polymer is about 10:1, about 9:1, about 8:1, about 7:1, about 6:1, about 5:1, about 4:1, about 3:1, about 2:1, about 1.85:1, about 1:1, about 1:2, about 1:3, about 1:4, about 1:5, about 1:5.6, about 1:6, about 1:7, about 1:8, about 1:9, or about 1:10.

The compositions of the present invention may further comprise a solvent. The solvent may be chosen from water, a cosmetically acceptable organic solvent, or a mixture of water and a cosmetically acceptable organic solvent. Cosmetically acceptable organic solvents may, in various embodiments, be water-miscible, e.g. a mixture capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

The solvent is added to the composition of the invention separately from the solvent present in the aqueous dispersions of the latex polymers of the invention and/or in the resin emulsions comprising the dispersion of particles of the at least one silicone non-acrylic latex polymer of the invention.

The solvent may be present in an amount ranging up to about 95%, such as from about 1% to about 90%, from about 5% to about 80%, or from about 10% to about 60% by weight, based on the total weight of the composition, including all ranges and subranges there between.

In at least certain exemplary embodiments, the latex polymer particles are not soluble in the solvent of the composition, and thus remain in particulate form even after evaporation of the solvent. For example, in embodiments where the composition comprises alcohol as a cosmetically acceptable organic solvent, the latex particles may remain in particulate form upon evaporation of the alcohol, such as when the composition is applied to a substrate.

Compositions according to various embodiments of the disclosure may further comprise additional components. Such components are known to those of skill in the art, or are within the ability of those of skill in the art to determine depending on the particular application, such as, for example, the particular component and/or amount thereof. Such components include, but are not limited to, wax dispersions, an oil phase containing fatty substances including oils, waxes and oil gellants, surfactants, film-forming polymers other than film-forming latex polymers, rheology modifiers, thickening agents, emulsifying agents, structuring agents, propellants, vitamins, plant extracts, propellants, shine agents, conditioning agents, and mixtures thereof.

In some embodiments, the wax dispersions that may additionally be present in the compositions of the present invention comprise particles having a volume-basis particle size distribution with peaks in the range of equal to or greater than 1 µm up to about 100 µm wherein the particles comprise at least one wax having a melting point of greater than 35° C., a surfactant mixture comprising a nonionic surfactant and an ionic surfactant, water, and optionally, an oil gellant.

In various exemplary embodiments, the wax dispersion can be prepared with a surfactant mixture comprising a combination of nonionic and ionic surfactants, and following an emulsification process.

The particles comprising the wax dispersion of the present invention may be chosen from particles of natural and synthetic waxes. Natural waxes may include, for example, one or a combination of animal, vegetable/plant, mineral, or petroleum derived waxes. They are typically esters of fatty acids and long chain alcohols. Wax esters are derived from a variety of carboxylic acids and a variety of fatty alcohols. The waxes comprising the solid wax particle of the present invention may also be known as solid lipids.

Examples of waxes comprising the particles of the wax dispersion of the present invention include, but are not limited to, beeswax, hydrogentated alkyl olive esters such as hydrogenated myristyl olive ester and hydrogenated stearyl olive ester (commercially available under the trade name phytowax olive), VP/eicosene copolymer, commercially available from the supplier ISP under the tradenames, Antaron® V 220 or Ganex® V 220F, carnauba wax, candelilla wax, ouricoury wax, Japan wax, cork fibre wax or sugar cane wax, rice wax, montan wax, paraffin wax, lignite wax or microcrystalline wax, ceresin or ozokerite, palm kernel glycerides/hydrogenated palm glycerides and hydrogenated oils such as hydrogenated castor oil or jojoba oil, sugarcane, retamo, bayberry, rice bran, soy, castor, esparto, japan waxes, hydroxyoctacosanyl hydroxystearate, Chinese wax, cetyl palmitate, lanolin, shellac, and spermaceti; synthetic waxes such as those of the hydrocarbon type and polyethylene waxes obtained from the polymerization or copolymerization of ethylene, and Fischer-Tropsch® waxes, or else esters of fatty acids, such as octacosanyl stearate, glycerides which are solid at temperatures of above 35° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane)tetrastearate, which is sold or manufactured by Heterene under the name HEST® 2T-4S, and mixtures thereof.

Other examples of waxes or solid lipids include C20-40 di- and triglycerides, including those which contain unsaturated fatty acids, C20-40 fatty alcohols, C2-40 fatty amines and their compounds, and sterols. Yet further examples include Hest 2T-5E-4S, Ditrimethylolpropane tetralaurate, Koster BK-34, Fluoro Polymethylalkyl dimethylsiloxane, Blend of Dilauryl Adipate and Ditetradecyl Adipate, Astrocaryum MuruMuru Seed Butter, *Myrica Pubescens* Wax, PEG-70 Mango Glycerides, oxypropylenated lanolin wax, and hydrogenated Coco-glycerides.

Other suitable waxes include silsesquioxane resin waxes such as C30-45 alkyldimethylsilyl propylsilsesquioxane, commercially available as DOW CORNING SW-8005 C30 Resin Wax, from the company Dow Corning and such as those described in WO2005/100444.

The amount of particles present in the wax dispersion according to various embodiments may range from about 10-60%, such as about 15-50%, about 20-45%, or about 25-40%, by weight, including all ranges and subranges therebetween, based on the weight of the wax dispersion.

The compositions may comprise an oil phase containing a fatty substance selected from oils, waxes, oil gellants, mixtures thereof. The oils include natural oils, plant oils and triglycerides.

As oils of plant origin or synthetic triglycerides that may be used in the composition of the invention as liquid fatty substances, examples that may be mentioned include:

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, camellia oil, olive oil, caprylic/capric acid triglycerides, for instance those sold by the company Stearineries Dubois or those sold under the names MIGLYOL 810, 812 and 818 by the company Dynamit Nobel, jojoba oil and shea butter oil.

Liquid fatty esters derived from monoalcohols or triglycerides of plant origin will preferably be used as esters according to the invention.

The oils may also be chosen from the organic solvents described above.

The wax(es) which may comprise the oil phase generally have a melting point of greater than 35° C. and are solid or semisolid at room temperature.

The waxes may be chosen from particles of natural and synthetic waxes. Natural waxes may include, for example, one or a combination of animal, vegetable/plant, mineral, or petroleum derived waxes. They are typically esters of fatty acids and long chain alcohols. Wax esters are derived from a variety of carboxylic acids and a variety of fatty alcohols.

The oil gellant may be selected from an oil gellant comprising at least one styrenic block copolymer, semicrystalline polymers, a glutamide-based compound, a polyamide, and mixtures thereof.

In various embodiments, the composition described herein may have a pH ranging from about 2 to about 9, such as about 3 to about 8, or about 4 to about 7, including all ranges and subranges there between.

Methods of Use

The compositions of the present invention may be applied onto substrates chosen from keratinous substrates such as hair.

Thus, in one embodiment, a method of coating a keratinous substrate such as hair or skin is provided, wherein said method involves applying onto the substrate, any one of the compositions of the present invention.

In certain embodiments, a method of shaping or altering the shape of hair is provided, wherein said method involves applying onto the hair, any one of the compositions of the present invention.

The term "shaping hair" as used herein can also mean changing the configuration of hair.

In certain other embodiments, a method of styling hair is provided, wherein said method involves applying onto the hair, any one of the compositions of the present invention In other embodiments, the application of an external stimuli such as physical force, for example, brushing or combing, onto the coated or treated substrate or hair may be desirable or required in order to impart additional benefits to the substrate or hair. The substrate may also be molded or shaped or positioned as desired while being subject to the external stimuli.

Thus, methods of coating a keratinous substrate such as hair, or shaping or altering the shape of hair, or styling hair are provided, wherein said method involves applying onto the substrate or hair, any one of the compositions of the present invention.

The terms "film," "coat" and "coating" as used herein with respect to the composition that is applied onto the surface of a substrate such as hair can be a continuous or a discontinuous film or coat that adheres to the substrate.

The term "discontinuous" means that there are breaks, gaps or interruptions in the film or coat produced when a composition of the present invention is applied onto a substrate.

The compositions of the present invention may especially constitute hair care compositions such as hair styling, hair straightening/relaxing, hair curling/perming/waving, and hair treatment products.

In at least certain exemplary embodiments, the compositions are in the form of hair styling compositions, in any form, such as, for example, a gel, a cream, a foam, a lotion, an emulsion, or a liquid that may be sprayed onto or otherwise applied to the hair. In various embodiments, the composition may be provided in the form of a gel, a mousse, or a spray. In at least certain embodiments, the composition may be applied to the hair by first applying the composition onto the hands, and then contacting the hair with the hands; in other embodiments, the composition may be applied directly onto the hair, such as by spraying or by use of an applicator (for example, bottle tip, spatula, comb or brush). The compositions may, in various embodiments, be applied to the hair as a leave-on treatment.

In various embodiments, the application of an external stimuli, such as physical force, for example, brushing or combing or running the fingers through the hair, may be desirable as part of the hair styling process. By way of example only, before, during, or after the composition is applied to wet or dry hair, the hair may be further treated with said external stimuli. In at least certain embodiments, the hair may also be shaped or positioned as desired while exposed to external stimuli.

The above-described methods of the present invention may additionally include a step of styling or shaping hair using a means for styling or shaping hair.

The above-described methods of the present invention allow one to shape/re-shape or re-position the hair on the head, such as to straighten the hair, curl the hair, redefine hair curl, or volumize the hair, and to repeat the steps of said method as many times as desired and without needing to re-apply the composition and/or re-wet the hair.

As described, compositions according to the disclosure may impart a film on a substrate, such as on the hair or on the hand during or after application to the hair. A film formed by the composition may, surprisingly, be clean-feeling and not sticky or not greasy, as with traditional hair care and styling products. Also surprisingly, the composition may impart a film on the hair that leaves the hair relatively natural and clean-feeling, yet has a flexible coating, leaving little to no residue, allows for the hair to be bouncy and springy with little to no frizz or flaking, may impart relatively high definition with individualized curls, style control, volume, and shine, and/or may allow for relatively long-lasting hold and style memory. Furthermore, in at least certain embodiments according to the disclosure, the compositions are not sticky or tacky. A user of hair compositions according to various embodiments described herein may thus feel that the composition is not perceptible or is "invisible," yet still effectively style and/or hold the hair. Additionally, the compositions may have effective hair styling and/or hold properties, even in conditions of high, or relatively high, humidity. In at least certain embodiments according to the disclosure, the compositions may be quick-drying, which may allow drying and/or styling time to be reduced, as well as further improve ease of styling and curl retention.

Furthermore, as described, compositions prepared according to various embodiments may provide for varying degrees of hold to be imparted to a hair style. By way of non-limiting example only, in order to obtain a spiky look to hair of a very short length, a high level of styling hold may be desirable. Or, as a further non-limiting example, in order to obtain a flowing look or to maintain hair curls for hair of medium length or longer length, a light to medium level of style hold may be desirable. By altering the weight amounts of the components of the composition of the invention and/or by varying weight ratios of the latex polymers (a) to each other and/or weight ratios of the latex polymers (a) to the silicone latex polymers, it is possible to formulate compositions having high levels of style hold, medium to high levels of style hold, medium levels of style hold, or light to medium levels of style hold.

In addition, hair styled or treated with compositions according to the disclosure may, in at least certain exemplary embodiments, be hydrophobic, and/or may appear less frizzy and/or may be less prone to breakage, relative to hair subjected to the same conditions but not having been styled or treated with a composition according to the disclosure.

The compositions of the present invention can be provided in a plethora of galenic forms, including but not limited to creams, liquid, gel, cream-gel, lotion, foam, serum, paste, semi-solid, solid stick, stick-gel, or a powder, and may be in the form of a mousse or a spray, and may optionally be packaged as an aerosol, prepared according to the usual methods.

In at least certain embodiments, a film formed by the compositions described herein may be clear and/or stable. In such embodiments, phase separation and dramatic aggregation of latex particles are minimized.

In addition, hair styled or treated with compositions according to the disclosure may, in at least certain exemplary embodiments, be hydrophobic, and/or may appear less frizzy and/or may be less prone to breakage, relative to hair subjected to the same conditions but not having been styled or treated with a composition according to the disclosure.

It should be noted, however, that compositions and films, as well as hair to which the composition or film has been applied, according to the disclosure may not have one or more of the herein-referenced properties, yet are intended to be within the scope of the disclosure.

Also disclosed herein are methods for styling the hair, said methods comprising applying a composition according to the disclosure to the hair (wet, dry or semi-dry), either before, during, or after styling the hair. One or more steps of treating the hair with an external stimuli, such as combing or brushing or running the fingers through the hair, before, during, or after the composition has been applied to the hair are also contemplated.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

It should be understood that the precise numerical values used in the specification and claims form additional embodiments of the disclosure, and are intended to include any ranges which can be narrowed to any two end points disclosed within the exemplary ranges and values provided, as well as the specific end points themselves. Efforts have been made to ensure the accuracy of the numerical values disclosed herein. Any measured numerical value, however, can inherently contain certain errors resulting from the standard deviation found in its respective measuring technique.

It should be understood that compositions according to various embodiments of the disclosure form a film or coating when applied to a substrate. However, the various properties of the film described herein are intended to include any film provided by compositions according to the disclosure, regardless of whether the film is attached or bonded to the substrate or not. By way of example only, once the compositions are applied to a substrate and a film is formed, the film may subsequently be removed in order to evaluate properties such as strain and Young's modulus.

EXAMPLES

The following Examples are intended to be non-restrictive and explanatory only, with the scope of the invention being defined by the claims.

Procedures

A. Procedure for Determination of Physical Properties of Films

Film plating: The film from the latex polymer(s) is obtained by allowing a 30 g water solution containing 4 g of the latex polymer(s) to dry in a 100 ml PFA Petri dish (100 mm diameter×15 mm height) at room temperature for at least 3 days.

Film measurement: The latex film, with known dimensions (length, width, thickness), is mounted on the Q800 Dynamic Mechanical Analysis from TA Instrument, and tested using in a DMA Control Force mode. The stress/strain test is performed using the following procedure:

Preload force: 0.001 N
Isothermal: 25° C.
Soak time: 0 min
Force ramp rate: 0.1 N/min to 18 N The test ends when the sample breaks, 18 N force is reached, or maximum displacement is achieved (25.5 mm).

From the stress/strain curve, the Young's Modulus is calculated as the slope of the linear portion at about 0.01% Strain to about 1% Strain. The % Strain at the stress of 10 Pa is also reported.

A high Young's Modulus represents a hard film, a low Young's Modulus represents a soft film. A high Strain represents a stretchy film, a low Strain represents a brittle film.

In accordance with the present invention, by associating various non film-forming and/or film-forming latex polymers chosen from polyurethane latex polymers and acrylate latex polymers with silicone latex polymers at different ratios, varying mechanical properties (i.e. stiffness and flexibility) of the films or coatings formed could be obtained which can be useful to suit different hair styling/shaping applications and to obtain different cosmetic attributes such as, the type and level of hold on hair or the feel of the hair. When a resulting film is formed, the film has a Young's modulus of up to 1 GPa, and a % strain at the stress of 10 Pa of less than 70%.

B. Procedure for Durability Determination Using High Humidity Curl Retention (HHCR) Test Hair Treatment Regular bleached hair swatch (from HIP, 14.5 cm long, about 0.5 g) is treated with solutions of 3% by weight of active material of latex polymer (acrylate latex polymer and/or polyurethane latex polymer and/or silicone latex polymer), based on the total weight of the solution (0.5 g solution/g hair). The hair is combed until the solution is uniformly distributed over the hair swatch surface. The treated hair is then rolled onto a spiral rod (0.5 in diameter) and allowed to dry at room temperature overnight.

Curl Retention Measurement

The coiled hair is removed from the rod and placed in the humidity chamber at 95% RH, 25° C. for 24 hours. % Curl Retention was calculated using the formula below:

$$\% \text{ Curl Retention} = \frac{(Lo - Lt)}{(Lo - Li)} * 100$$

Where:
Lo=Original hair length (fully extended hair length)
Li=Initial hair length (length of hair before humidity exposure)
Lt=Length of hair after 24 hr humidity exposure Example 1

Physical Properties of Films from the Associations of Divinyldimethicone/Dimethicone Copolymer (in Dow Corning HMW 2220, Silicone Latex Polymer) and Film Forming Latex Polymer Homogeneous films were obtained from the association of Dow Corning HMW 2220 non-ionic latex and various latex polymers at various polymer weight ratios. The physical properties of the films are shown below.

TABLE 1

| Sample | Young's Modulus (MPa) | Strain at 10 Pa (%) |
|---|---|---|
| DC HMW 2220 | Not a film former | |
| DC HMW 2220:LUVIFLEX SOFT 3:1 | 0.34 | 7.17 |
| DC HMW 2220:LUVIFLEX SOFT 1:1 | 110.01 | <0.001 |
| DC HMW 2220:LUVIFLEX SOFT 1:3 | 576.1 | <0.001 |
| LUVIFLEX SOFT | 790.3 | <0.001 |
| DC HMW 2220 | Not a film former | |
| DC HMW 2220:BAYCUSAN C1001 3:1 | 0.05 | 19.84 |
| DC HMW 2220:BAYCUSAN C1001 1:1 | 0.18 | 5.15 |
| DC HMW 2220:BAYCUSAN C1001 1:3 | 0.51 | 1.91 |
| BAYCUSAN C1001 | 1.39 | 0.72 |
| DC HMW 2220 | Not a film former | |
| DC HMW 2220::DAITOSOL 5000 SJ 3:1 | 0.02 | 46.57 |
| DC HMW 2220::DAITOSOL 5000 SJ 1:1 | 0.05 | 26.79 |
| DC HMW 2220::DAITOSOL 5000 SJ 1:3 | 0.07 | 10.51 |
| DAITOSOL 5000 SJ | 0.76 | 1.56 |
| DC HMW 2220 | Not a film former | |
| DC HMW 2220:NEOREZ R-2202 3:1 | 0.54 | 3.08 |
| NEOREZ R-2202 | Film too brittle to be measured | |
| DC HMW 2220:LUVIFLEXSOFT:BAYCUSAN C1001 1:1:1 | 3.36 | 0.31 |
| DC HMW 2220:DAITOSOL 5000 SJ:NEOREZ R-2202 1:1:1 | 2.82 | 0.38 |

DC HMW 2220, aqueous dispersion containing about 60% by weight of divinyldimethicone/dimethicone copolymer and $C_{12}$-$C_{13}$ Pareth-3 and $C_{12}$-$C_{13}$ Pareth-23

BAYCUSAN C1001, aqueous dispersion containing 32+/−2% by weight polyurethane-34

DAITOSOL 5000 SJ, Acrylates/ethylhexyl acrylate copolymer, about 50% by weight of solids/active material, NEOREZ R-2202, polyurethane, about 35% by weight of solids/active material LUVIFLEX SOFT, aqueous dispersion containing about 30%% by weight acrylates copolymer Example 2

Physical Properties of Films from the Associations of Polymethylsiloxane Resin (in BLUESIL BP 9878 Resin Emulsion, Silicone Latex Polymer) and Film Forming Latex Polymer Homogeneous films are obtained from the association of BLUESIL BP 9878 latex polymer and various latex polymers at various polymer weight ratios. Their physical properties are shown below.

TABLE 2

| Sample | Young's Modulus (MPa) | Strain at 10 Pa (%) |
|---|---|---|
| BLUESIL BP 9878 | 0.99 | 0.74 |
| BLUESIL BP 9878:LUVIFLEX SOFT 3:1 | 29.68 | 0.3 |
| BLUESIL BP 9878:LUVIFLEX SOFT 1:1 | 479.4 | 0.005 |
| BLUESIL BP 9878:LUVIFLEX SOFT 1:3 | 643.02 | <0.001 |
| LUVIFLEX SOFT | 790.3 | <0.001 |
| BLUESIL BP 9878 | 0.99 | 0.74 |
| BLUESIL BP 9878:BAYCUSAN C1001 3:1 | 0.33 | 0.62 |
| BLUESIL BP 9878:Baycusan C1001 1:1 | 0.42 | 0.53 |
| BLUESIL BP 9878:BAYCUSAN C1001 1:3 | 1.08 | 0.69 |
| BAYCUSAN C1001 | 1.39 | 0.72 |
| BLUESIL BP 9878 | 0.99 | 0.74 |
| BLUESIL BP 9878:DAITOSOL 5000 SJ 3:1 | 0.15 | 6.01 |
| BLUESIL BP 9878:DAITOSOL 5000 SJ 1:1 | 0.16 | 6.85 |
| BLUESIL BP 9878:DAITOSOL 5000 SJ 1:3 | 0.24 | 4.16 |
| DAITOSOL 5000 SJ | 0.76 | 1.56 |
| BLUESIL BP 9878 | 0.99 | 0.74 |
| Bluesil:NEOREZ R-2202 3:1 | 45.95 | 0.02 |
| NEOREZ R-2202 | Film too brittle to be measured | |
| BLUESIL BP 9878:LUVIFLEX SOFT:BAYCUSAN C1001 1:1:1 | 34.67 | 0.08 |
| BLUESIL BP 9878:DAITOSOL 5000 SJ:NEOREZ R-2202 1:1:1 | 11.28 | 0.11 |

Example 3

High Humidity Curl Retention (See Procedure B Above)

High humidity curl retention studies on hair treated with solutions containing the latex film-forming polymer or the silicone latex polymer or the association of latex polymer and silicone latex polymer were performed as described above.

TABLE 3

| TREATMENT | % Curl Retention | Softness Rating* |
|---|---|---|
| BAYCUSAN C1001 | 96.9% | − (hard) |
| DC HMW 2220 | 43.8% | ++ (softest) |
| DC HMW 2220:BAYCUSAN C1001 1:3 weight ratio | 90.3% | + (softer) |

*Softness ratings:
hard indicates a strong, smooth film, but no conditioning feel on hair; non-tacky/non-sticky feel
softest indicates that there does not seem to be a film on hair and composition feels tacky or sticky on hair
softer indicates a conditioning, smoother and softer feel on hair; non-tacky/non-sticky feel; very good hair quality or feel to the touch Hair treated with the combination of silicone latex polymer and film forming latex polymer displayed both a high styling property over time and at high humidity condition as indicated by the high curl retention value and at the same time, a good conditioned state as indicated by the softness rating of "softest". In contrast, while hair treated with the silicone latex polymer alone demonstrated a softness rating of "softer", it demonstrated a much lower curl retention value, indicating significantly less styling hold over time and at high humidity (about 2 times lower). In addition, while the hair treated with the latex polymer alone showed a high curl retention value over time and at high humidity, the hair was significantly less conditioned as indicated by the softness rating of "hard", i.e., the hair felt hard/no conditioning feel to the touch.

It is to be understood that the foregoing describes preferred embodiments of the invention and that modifications may be made therein without departing from the spirit or scope of the invention as set forth in the claims.

What is claimed is:
1. A hair styling composition comprising:
   (a) (1) latex polymer A having a Young's modulus ranging from about 0.1 MPa to about 10 MPa, and a strain, under stress at 0.5 MPa, of at least about 1%, wherein latex polymer A is Acrylates copolymer, Acrylates/Ethylhexyl Acrylate copolymer, Acrylates/VA copolymer, Polyurethane-34, Polyurethane-32, or Polyurethane-48; and
   (2) latex polymer B having a Young's modulus ranging from about 10 MPa to about 6 GPa, and a strain, under stress at 0.5 MPa, of less than about 5%, wherein latex polymer B is Acrylates copolymer, Polyacrylate-2 crosspolymer, Styrene/Acrylic copolymer, Polyurethane-35, Polyurethane-1, Polycarbamyl Polyglycol Ester, Styrene/Acrylates Copolymer, or Styrene/Acrylates/Ammonium Methacrylate Copolymer;
   wherein latex polymers A and B are dispersed particles in an aqueous dispersion medium;
   (b) a dispersion of particles of at least one silicone latex polymer, wherein the silicone latex polymer is formed from (i) dimethylvinylsiloxypolydimethylsiloxane and (ii) organohydropolysiloxane of formula (II):

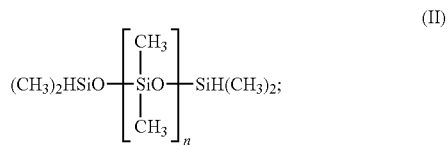

wherein n ranges from 15 to 25;
and optionally,
(c) a solvent;
wherein the weight ratio of the at least one silicone latex polymer (b) to the latex polymers (a) ranges from about 10:1 to about 1:10; and
wherein the composition produces a film having a Young's modulus ranging up about 1 GPa, and a strain, under stress at 10 MPa, of less than about 70%.

2. The hair styling composition of claim 1, wherein the latex polymers A and B are present in a combined amount ranging from about 0.1% to about 30% by weight, based on the total weight of the composition.

3. The hair styling composition of claim 1, wherein the at least one silicone latex polymer (b) is present in an amount ranging from about 0.1% to about 30% by weight, based on the total weight of the composition.

4. The hair styling composition of claim 1, wherein the weight ratio of the at least one silicone latex polymer (b) to the latex polymers A and B ranges from about 3:1 to about 1:3.

5. The hair styling composition of claim 4, wherein the weight ratio of the at least one silicone latex polymer (b) to the latex polymers A and B is about 1:1.

6. The hair styling composition of claim 1, wherein the aqueous dispersion medium further comprises $C_{12}$-$C_{13}$ Pareth-3 and $C_{12}$-$C_{13}$ Pareth-23.

7. The hair styling composition of claim 1, wherein the latex polymers A and B are polyurethane latex polymers.

8. The hair styling composition of claim 1, wherein the latex polymers A and B are acrylate latex polymers.

9. The hair styling composition of claim 1, wherein the latex polymers A and B comprise a acrylate latex polymer and a polyurethane latex polymer; wherein when polymer A is an acrylate latex polymer, polymer B is a polyurethane latex polymer; and when polymer A is a polyurethane latex polymer, polymer B is an acrylate latex polymer.

10. The hair styling composition of claim 9 wherein the latex polymers A and B are present in a combined amount ranging from about 0.25% to about 10% by weight, based on the total weight of the composition.

11. The hair styling composition of claim 1, wherein the weight ratio of latex polymers A:B ranges from about 10:1 to about 1:10.

12. The hair styling composition of claim 11, wherein the weight ratio of latex polymers A:B ranges from about 1:5 to about 5:1.

13. The hair styling composition of claim 12, wherein the weight ratio of latex polymers A:B is about 1:1.

14. The hair styling composition of claim 1, wherein the composition further comprises a solvent (c) selected from water, at least one organic solvent, and mixtures thereof.

15. The hair styling composition of claim 1, further comprising at least one additional component selected from wax dispersions, oils, surfactants, film-forming polymers other than film-forming latex polymers, rheology modifiers, thickening agents, emulsifying agents, structuring agents, propellants, vitamins, plant extracts, propellants, shine agents, conditioning agents, and mixtures thereof.

16. A method of styling hair comprising: (i) applying the hair styling composition of claim 1 onto hair; and (ii) optionally, using a means for styling the hair.

17. A method of making a hair styling composition, the process comprising:

A. combining:
- (a) (1) latex polymer A having a Young's modulus ranging from about 0.1 MPa to about 10 MPa, and a strain, under stress at 0.5 MPa, of at least about 1%, wherein latex polymer A is Acrylates copolymer, Acrylates/Ethylhexyl Acrylate copolymer, Acrylates/VA copolymer, Polyurethane-34, Polyurethane-32, or Polyurethane-48; and
- (2) latex polymer B having a Young's modulus ranging from about 10 MPa to about 6 GPa, and a strain, under stress at 0.5 MPa, of less than about 5%, wherein latex polymer B is Acrylates copolymer, Polyacrylate-2 crosspolymer, Styrene/Acrylic copolymer, Polyurethane-35, Polyurethane-1, Polycarbamyl Polyglycol Ester, Styrene/Acrylates Copolymer, or Styrene/Acrylates/Ammonium Methacrylate Copolymer;

wherein latex polymers A and B are dispersed particles in an aqueous dispersion medium;

- (b) a dispersion of particles of at least one silicone latex polymer, wherein the silicone latex polymer is formed from (i) dimethylvinylsiloxypolydimethylsiloxane and (ii) organohydropolysiloxane of formula (II):

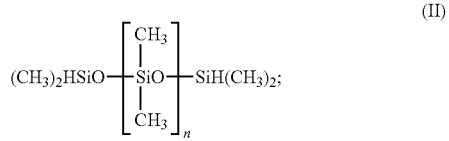

wherein n ranges from 15 to 25;

and optionally, (c) a solvent;

wherein the weight ratio of the at least one silicone latex polymer (b) to the latex polymers A and B ranges from about 10:1 to about 1:10; and B. mixing the components in (A) in order to form the hair styling composition; and wherein the composition produces a film having a Young's modulus ranging up about 1 GPa, and a strain, under stress at 10 MPa, of less than about 70%.

* * * * *